US010521722B2

(12) United States Patent
Bialk et al.

(10) Patent No.: US 10,521,722 B2
(45) Date of Patent: Dec. 31, 2019

(54) DISTURBANCE DETECTION, PREDICTIVE ANALYSIS, AND HANDLING SYSTEM

(71) Applicant: Quietyme Inc., Neshkoro, WI (US)

(72) Inventors: John Bialk, Neshkoro, WI (US); David Hussein Zoroufy, Middleton, WI (US)

( * ) Notice: Subject to any disclaimer, the term of this patent is extended or adjusted under 35 U.S.C. 154(b) by 342 days.

(21) Appl. No.: 14/676,549

(22) Filed: Apr. 1, 2015

(65) Prior Publication Data
US 2015/0278690 A1 Oct. 1, 2015

Related U.S. Application Data

(60) Provisional application No. 61/973,587, filed on Apr. 1, 2014.

(51) Int. Cl.
| | |
|---|---|
| *G06N 5/02* | (2006.01) |
| *G01H 17/00* | (2006.01) |
| *G06F 16/68* | (2019.01) |
| *G06F 16/951* | (2019.01) |
| *G06Q 10/06* | (2012.01) |
| *G06Q 50/22* | (2018.01) |

(52) U.S. Cl.
CPC ............ *G06N 5/022* (2013.01); *G01H 17/00* (2013.01); *G06F 16/686* (2019.01); *G06F 16/951* (2019.01); *G06Q 10/06* (2013.01); *G06Q 50/22* (2013.01)

(58) Field of Classification Search
None
See application file for complete search history.

(56) References Cited

U.S. PATENT DOCUMENTS

| | | |
|---|---|---|
| 7,019,637 B1 | 3/2006 | Johnson et al. |
| 7,796,029 B2 | 9/2010 | Ma et al. |
| 7,843,336 B2 | 11/2010 | Kucharyson et al. |
| 8,111,156 B2 | 2/2012 | Song et al. |
| 8,395,510 B1 | 3/2013 | Kirk et al. |
| 8,587,414 B2 | 11/2013 | Bandyopadhyay et al. |

(Continued)

FOREIGN PATENT DOCUMENTS

WO 2005038738 4/2005

OTHER PUBLICATIONS

International Search Report and Written Opinion dated Jun. 26, 2015 for Intl. Appln. No. PCT/US2015/023913.
(Continued)

*Primary Examiner* — James G Norman

(57) ABSTRACT

A disturbance detection, predictive analysis, and handling system and method is provided. The system and method may assist in identifying when, how, and what actions should be taken and by whom to prevent, reduce, or eliminate disturbances. The system and method may do so by monitoring or sensing activity in real time, performing predictive analytics on the data, and communicating the outcome to achieve a desired result. The system and method may include sensors provided within a sensor unit in communication with a hub. The sensor unit and hub may communicate over a personal area network. The system and method may also include a server and analytics engine to aid in the identification of disturbance and/or damage. The system and method may also use predictive algorithms and historic disruption data to enhance the accuracy of its prediction of disturbance and/or damage.

19 Claims, 9 Drawing Sheets

(56) References Cited

U.S. PATENT DOCUMENTS

| | | | |
|---|---|---|---|
| 8,624,729 B2 | 1/2014 | Preden et al. | |
| 8,644,166 B2 | 2/2014 | Xia et al. | |
| 10,014,003 B2 | 7/2018 | Kim et al. | |
| 2004/0236466 A1* | 11/2004 | Ota | G08B 17/10 |
| | | | 700/245 |
| 2006/0089542 A1* | 4/2006 | Sands | G06F 19/00 |
| | | | 600/300 |
| 2009/0093978 A1* | 4/2009 | Sadri | C21B 7/12 |
| | | | 702/56 |
| 2009/0303042 A1* | 12/2009 | Song | G08B 13/19647 |
| | | | 340/566 |
| 2010/0025483 A1* | 2/2010 | Hoeynck | H02J 3/14 |
| | | | 236/1 C |
| 2010/0201515 A1* | 8/2010 | Fleming | H04L 67/125 |
| | | | 340/539.23 |
| 2011/0093220 A1* | 4/2011 | Yang | G01M 3/243 |
| | | | 702/51 |
| 2014/0207280 A1* | 7/2014 | Duffley | G05D 1/0016 |
| | | | 700/257 |

OTHER PUBLICATIONS

International Preliminary Report on Patentability dated Oct. 13, 2016 for Intl. Appln. No. PCT/US2015/023913.

* cited by examiner

DISTURBANCE DETECTION, PREDICTIVE ANALYSIS, AND HANDLING SYSTEM

CROSS-REFERENCE TO RELATED APPLICATIONS

This application claims the benefit of U.S. Provisional Patent application No. 61/973,587 entitled "Disturbance Detection, Predictive Analysis, and Handling System" filed Apr. 1, 2014, which is hereby incorporated by reference.

FIELD

The present inventions relate to the field of detection and alert systems. The present inventions more specifically relate to the field of detection, predictive analysis, and handling of a disturbance or potential disturbance.

BACKGROUND

The reduction of noise disturbances in various medical, commercial, and residential settings is of significant importance. For example, the importance of reducing noise disturbances in hospitals and improving patient sleep experience has been well documented in medical journals, which have demonstrated a correlation between sleep experience and medical outcome. According to hospital survey results, such as the HCAHPS survey, the lowest score nationally is in response to how quiet the area around the patient's room was during the night. Not only does this noise and disturbance affect the health of the patient, but also Medicare uses the results of these surveys to determine the amount of money a hospital is to be reimbursed for patients using Medicare. If the hospital's results are below the national average, they receive a lower payment, while survey results above the national average result in a higher payment.

While a hospital/medical/healthcare facility is described for purposes of example, in addition to medical or healthcare facilities, the hospitality industry also has a significant need to reduce disturbances to guests and, in particular, to guest sleep experiences. A common complaint is noise that results in the disturbance of guests in neighboring rooms, which can lead to a poor guest experience and subsequently a loss of business.

Likewise, multi-family residential facilities have a need to reduce disturbances of tenants/occupants for similar reasons. A means of predicting damage in the management of a facility is also of particular importance.

Accordingly, what is needed is a system which can detect and predict a disturbance, such as to a sleep experience, or detect and predict damage to a facility, and to identify when, how, and what actions should be taken to prevent, reduce, or eliminate these disturbances or damage.

SUMMARY

Accordingly, a disturbance detection, predictive analysis, and handling system is provided. The system described herein may assist in identifying when, how, and what actions should be taken and by whom to prevent, reduce, or eliminate disturbances. The system described herein may do so by monitoring or sensing activity in real time, performing predictive analytics on the data, and communicating the outcome to achieve a desired result. The system may include sensors and networks to aid in the identification of disturbance and/or damage. The system may also use predictive algorithms and historic disruption data to enhance the accuracy of its prediction of disturbance and/or damage.

In one illustrative example of implementation of the system, a system may be used in a hospital or assisted living facility for predicting disturbances to patient sleep experience through the use of various sensors. The system may identify when and what actions should be taken, and by whom, to prevent, reduce or eliminate these disturbances. In an alternative example of embodiments, the system may predict disturbances in the hospitality industry to guest sleep experiences. The system in this example may identify when, how, and what actions should be taken and by whom to prevent, reduce, or eliminate these disturbances. In another alternative example of embodiments, the system may predict disturbances to tenant/occupant sleep experience in a multi-family residential setting. The system may identify when, how, and what actions should be taken and by whom to prevent, reduce or eliminate these disturbances. In a further example of embodiments in facility management, the system may predict damage to a facility and identify when, how, and what actions should be taken and by whom to prevent, reduce, or eliminate this damage.

The system may use one or more sensors to read environmental data such as ambient temperature, noise, humidity, or light. The sensors may be provided in a sensor unit. The sensor unit may be placed in strategic positions throughout a building. For example, in patient rooms at a hospital. The sensor units may report to a central hub, which sends information to a server for processing and prediction. The server may identify or anticipate potential disruptions from the sensor data and alert personnel. Further analytics may be provided using a data analytics engine. The data analytics engine may create a data pattern or signature from the data and compare it with historical data signatures. Using these and other techniques, the data processing/analytics engine may provide a predictive report to users for disruption tracking and anticipation.

A disturbance detection, predictive analysis, and handling system is disclosed, including a sensor unit having a sound sensor and one or more network communication devices, the sensor unit having a processor programmed to transmit sensor data using the network communication device; a hub having one or more network communication devices, a processor, and data storage component, wherein the processor is programmed to accept and transmit the sensor unit data; a server having a network communication device, processor, and database, wherein the processor is programmed to analyze the sensor unit data; and a reporting device having a reporting software, the reporting device having a network communication device; wherein the network communication devices of the sensor unit, hub, and reporting device are selected from the group of Zigbee, Bluetooth, Wi-Fi, mobile broadband modem, or Ethernet.

A disturbance detection, predictive analysis, and handling method is disclosed, the method comprising: providing one or more sensors including a sound sensor within a first networked device in a first location; using one or more sensors provided within the first networked device to obtain a first group of sensor reads over a period of time; determining a first example value from the first group of sensor reads using the first networked device; transmitting the first example value from the first networked device to a first hub device; providing one or more sensors including a sound sensor within a second networked device in a second location; using one or more sensors provided within the second networked device to obtain a second group of sensor reads over a period of time; determining a second example value from the second group of sensor reads using the second networked device; transmitting the second example value from the second networked device to the first hub device; transmitting the first example value and second example value to a server; analyzing the first example value and second example value against one or more thresholds; transmitting an alert signal to an alert device; and saving the first example value and second example value to create historical data.

A disturbance detection, predictive analysis, and handling system is disclosed, the system comprising: a plurality of sensor devices that transmit data to one or more sensor hubs, each sensor device having: a sound sensor, a unique identifier, a personal area network identification, a personal area network communication device, and a microprocessor programmed to determine a highest sound value over a period of time; one or more sensor hubs that accept data from the plurality of sensor devices to a server, each sensor hub having: a sound sensor, a unique identifier, a personal area network identification, a personal area network communication device, a network communication device, and a microprocessor programmed to determine a highest sound value over a period of time and to send sensor values from the plurality of sensor devices to a server using the network communication device; a server which accepts data from the one or more sensor hubs, the server having: a network communication device, a database, and a processor programmed to execute an alert algorithm; a dashboard which accepts data from the server, the dashboard having: a network communication device, and a user interface displaying sensor data; and a data analytics engine that accepts data from the server, the data analytics engine having: a network communication device, a database containing historic sensor data and user-provided data, and a processor programmed to execute analysis algorithms.

These and other features and advantages of devices, systems, and methods according to this invention are described in, or are apparent from, the following detailed descriptions of various examples of embodiments.

BRIEF DESCRIPTION OF DRAWINGS

Various examples of embodiments of the systems, devices, and methods according to this invention will be described in detail, with reference to the following figures, wherein.

Figure 1:
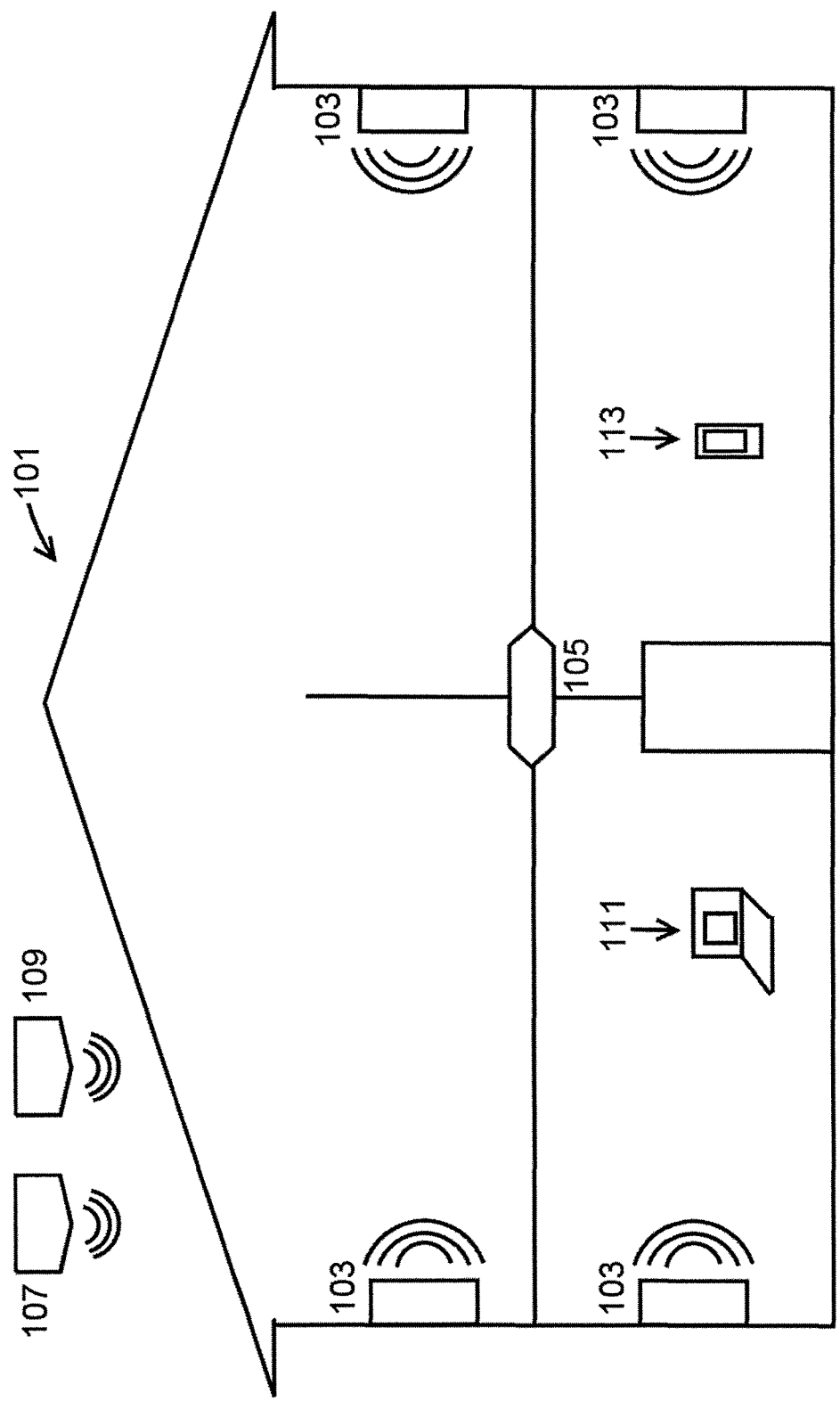
FIG. 1 is a representation of an embodiment of a system implemented in a building.

It should be understood that the drawings are not necessarily to scale. In certain instances, details that are not necessary to the understanding of the invention or render other details difficult to perceive may have been omitted. It should be understood, of course, that the invention is not necessarily limited to the particular embodiments illustrated herein.

DETAILED DESCRIPTION

The system 101 may be comprised in various embodiments of five primary (non-limiting) components: sensor unit 103, hub 105, server 107, data analytics engine 109, and dashboard 111. Additional features such as an alert device 113, input device 115, experiential data 157, and prediction reports 159 may likewise be included. It should be understood that while the figures may disclose a certain number of units, hubs, servers, etc., any appropriate number of components may be used. For example, many sensor units may be used with one hub, many hubs may be used with one remote server, many dashboards may be used with multiple sensor units and hubs, etc. It should also be understood certain components may be removed or combined—for example, removal of the data analytics engine or provision of the data analytics engine within the server.

FIG. 1 shows an example scenario where a system 101 according to one or more examples of embodiments may be used. In FIG. 1, sensor units 103 are provided throughout a building, a hub 105 is provided in a central location in the building, and a server 107 and data analytics engine 109 are provided externally. Devices displaying the dashboard 111 or alert devices 113 may also be provided. As will be further described herein, the sensor units 103 may use sensors to detect various attributes about the surrounding environment, transmit those attributes to the hub 105, which will transmit the acquired data to a server 107 which may relate data to an alert device 113 or dashboard 111. The data may also be sent to a data analytics engine 109.

Figure 2:
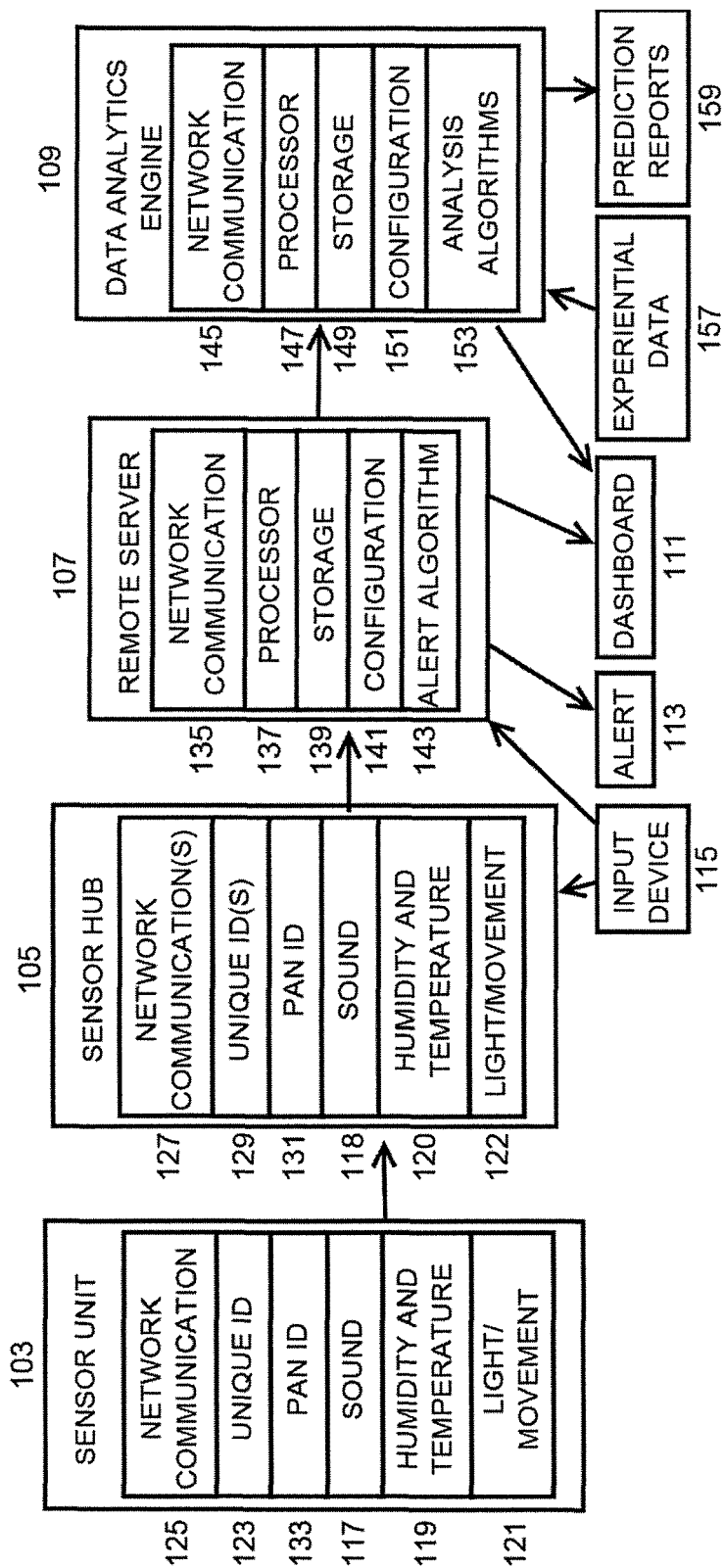
FIG. 2 is a logical flow diagram between the parts of an example embodiment of the system.

FIG. 2 shows some of the contents of the primary components of the system and how information may progress from sensor unit 103 to hub 105 to server 107 and onward to a data analytics engine 109, dashboard 111, alert device 113, or prediction report 159. It should be understood each component may include a processor which is programmed to complete the component's respective steps described herein.

As shown, the sensor unit 103 is provided with a number of components, including sensors 117/119/121, a unique identifier 123, and network communication 125. The unit 103 also has sensors, which may include (but is not limited to) a sound sensor 117, a temperature and/or humidity sensor 119, and a light sensor 121. It should be understood that these three sensor types are example sensors for use in the system, and different types of sensors may be added (or the example sensors removed) depending on the application of the sensor system. The sensors 117/119/121 each may use mechanisms to measure designated information from the environment. The sensors may gather this information with varied frequency. For example, the sensor unit may be configured to require the sound sensor 117 to obtain a sound sample every second, whereas the temperature and/or humidity sensor 119 may be configured to measure samples much less frequently, for example once every ten seconds. In various embodiments, the sound sensor 117 may measure the sound in the area surrounding the device once every millisecond and take the highest read data each second. In other words, each sensor unit may measure the decibel level a thousand times per second and identify the highest decibel for that second. The particular frequency of information obtained and how it may be obtained may be stored in sensor unit 103 firmware as programmed by the manufacturer or altered and updated through the network, for example, to reflect a security update or user preferences.

Figure 8:
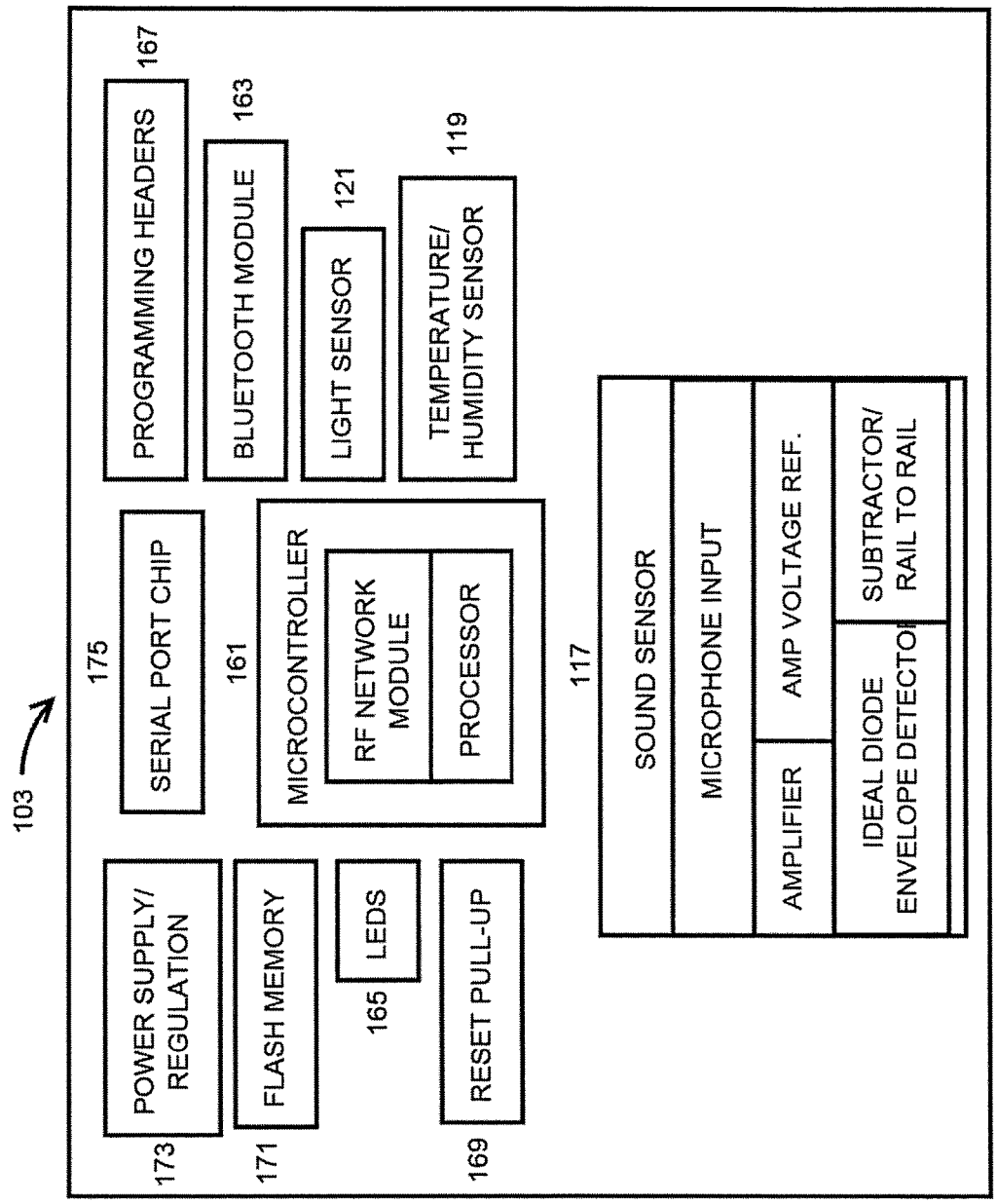
FIG. 8 is a block schematic representation of an example sensor unit.

The composition of the sensor unit 103 is shown in further detail in FIG. 8. As shown, a sensor unit 103 may be comprised of externally visible components such as light-emitting diodes (LEDs) 165, a power supply 173, reset 169, and housing (not shown). In various embodiments, the sensor unit may have a unitary body (housing) with a pronged outlet engagement, whereby the unit sits flush with a wall and is plugged into a standard outlet. In another embodiment, the sensor unit may include a power supply adaptable with a universal serial bus (USB) plug (mini, micro, standard, etc.). In other embodiments, the power mechanism may include an external transformer with a cord, or a plug and corresponding external jack. In another embodiment, the sensor unit 103 may be powered by a lithium ion or other type of battery. Combinations of the foregoing and other appropriate known charging mechanisms may also be used. Likewise, the sensor unit 103 may include a voltage regulation circuit to supply proper power to the unit components.

In various embodiments, the sensor unit 103 may include a temperature/humidity sensor 119, a light sensor 121, and a sound sensor 117. The sound sensor may include a variety of other components to allow for accurate sound readings, including a microphone input, amplifier, amplifier voltage reference, ideal diode envelope detector, and subtractor/rail-to-rail. These are non-limiting examples of components to allow for accurate and useful sound measurement. In various embodiments, the sensor unit 103 may further include one or more network communication mechanisms. For example, the unit may include a radio frequency network module embedded on the microcontroller 161 as well as a Bluetooth module 163. Both of these modules may be used, for example, to generate a mesh wireless transaction network such as a personal area connection. The sensor unit may include various information storage devices, for example, flash memory 171. In various embodiments, the sensor unit 103 may also include one or more programming headers 167 and one or more serial port chips 175 that are used in connection with a controller for (for example) bi-directional communication.

In order to send the acquired ambient information to another device, as shown above, the sensor unit 103 may include a network communication device 125 such as, but not limited to, a radio communication device (Zigbee, Bluetooth, Wi-Fi, mobile broadband modem) or wired communication device such as Ethernet. In various embodiments, the sensor unit 103 may be configured to transmit raw data to a hub 105. In the non-limiting example above, the sound sensor 117 on the sensor unit 103 measures the surrounding decibel level one thousand times per second, identifying and keeping the highest decibel for that second. The sensor unit may, for example, be configured to send information to the hub 105 every two seconds; therefore, the sensor unit may create and send a data packet including two readings (the highest sampled level in each of those two seconds) to the hub 105.

Using a processor and onboard memory (such as flash memory), the sensor unit 103 may gather the sensor data, provide a time stamp associated with the time the sensor data was obtained, provide a unique identification code 123, and send the data, time, and associated code 123 in one or more data packets to the sensor hub 105 by way of the network communication device 125. In various embodiments, the sensor unit(s) 103 may be configured to only connect with one particular hub. This may be facilitated by using only a particular radio band, password, or other appropriate means such as a personal area network identification (PAN ID) 133 which may correspondingly be saved on the sensor unit 103. This PAN ID 133 may correspond with a PAN ID provided on the hub 131. The sensor unit 103 may also have lights such as LEDs to indicate its connectivity status.

The sensor hub 105 may have one or more network communication devices 127, a unique device identifier (unique ID) 129, and a PAN ID 131. The sensor hub 105 may also include sensor components 118/120/122. The network communication devices 127 may include one or more types of radio communication devices (Zigbee, Bluetooth, Wi-Fi, mobile broadband modem) or wired communication device such as Ethernet. For example, the sensor hub may have a Zigbee, Ethernet, and Wi-Fi network communication device. The sensor hub 105 may also have memory including RAM or flash memory. Likewise, the sensor hub 105 may include a programmable microcontroller, such as a Raspberry Pi. The sensor hub 105 may be configured to use its sensors, which may include (but are not limited to) a sound sensor 118, temperature and/or humidity sensor 120, and light sensor 122 in much the same way as a sensor unit 103. As such, looking at FIG. 1, the sensor hub 105 may be used to also obtain sensor data in a central location in the building.

Much of the logic of the system may take place at the server 107 level. In various embodiments, the server may have one or more of the following: a wireless or wired network communication device 135 such as an Ethernet connection, a processor 137, storage 139 (for example, a database), configuration parameters 141, and a programmed alert algorithm 143, among other programmed components, which may include a restful opportunities calculator. For example, the server may be a remote cloud server having storage and processing hardware, such as high frequency Intel Xeon processors and SSD storage. The server may be of any suitable type, for example, Linux (including but not limited to Red Hat and SUSE) or Windows.

Similarly, the data analytics engine 109 may include one or more of the following: a network communication device 145, processor 147, storage 149, configuration 151, and analysis algorithms 153. The processor and storage may be any suitable programmable hardware or data structure, for example, a relational database.

The remote server 107 and data analytics engine 109 may report results to a variety of output devices such as, but not limited to, an alert device 113, user dashboard 111 or predictive reports 159. The alert device 113 may be a variety of devices, such as a cell phone, tablet, or other suitable device capable of receiving texts, emails, or other digital message means. The user dashboard 111 may be a website or application which may provide a graphical user interface displaying historical and predictive data, as well as alerts. Likewise, prediction reports 159 may be sent through the dashboard 111, email, or other suitable means.

The system may also accept input devices 115, which may be for configuration 155, to clear alerts, or input experiential data 157. This input device 115 may also house the dashboard 111. In various embodiments, the dashboard 111 itself may allow for inputs.

Figure 3:
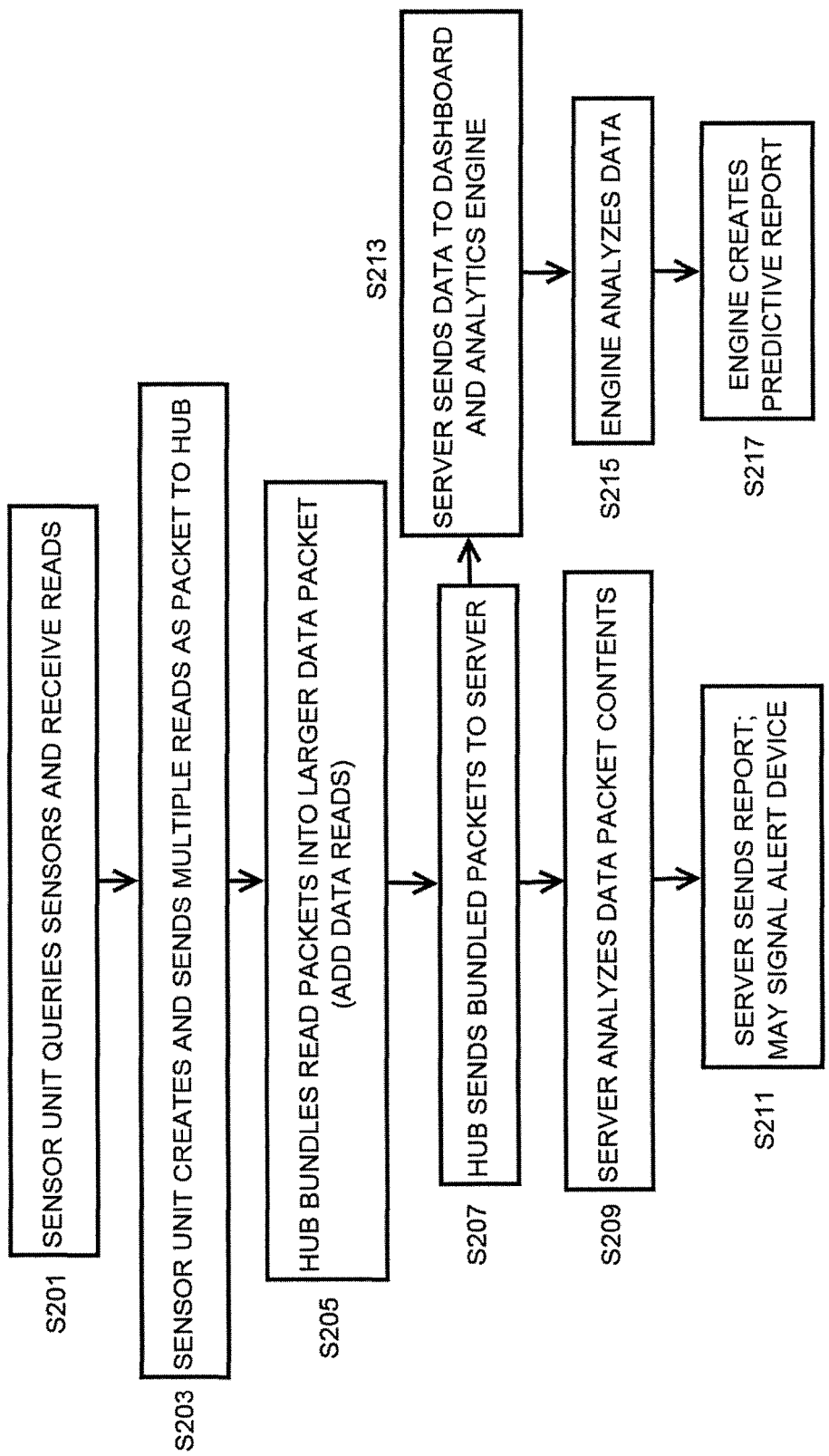
FIG. 3 is an example embodiment of a process executed by the system.

FIG. 3 describes the steps of an example simplified data flow from one component to the next. As shown in step S201 of FIG. 3, the sensor unit will query the sensors and receive the reads. Once these reads are received, the sensor unit 103 may determine an example value of each group of reads over a time period, and the example values for each time period may be sent to the hub S203. In various embodiments, the network communication device 125 may transmit the data packet to the hub 105 by way of other sensor units using a shortest-path algorithm (i.e. a "daisy chain" transmission). This transmission may append the prior module data to the next module's data, and so on until the hub is reached. In this way, the sensor unit module may act as a router, receiving another unit's data packet, appending its own packet, and routing the combined information to the appropriate next module.

The sensor hub 105 may receive the unit data, identifier 123, and timestamps from multiple devices. The hub 105 may aggregate the sensor data S205 (which may come from multiple sensor devices) and send the data in step S207 to a server 107. The hub 105 may have multiple data communication mechanisms 127. For example, the hub 105 may accept data from the sensor unit(s) 103 using a Bluetooth or Zigbee connection, while it may send data to a server 107 using a wireless card, Ethernet, or other suitable means. The hub 105 may be configured to only accept transmissions from certain sensor unit(s). For example, each sensor unit 103 may use a PAN ID that correlates with the PAN ID of the hub 105 in order to ensure transmission only between the hub 105 and its associated units 103. Such a configuration can allow for multiple networks in buildings across multiple floors, for example, without confusing the location of the sensor unit(s) 103. The configuration of the sensor unit 103 and hub 105 may be over a relatively large area, for example, a 75-foot indoor distance between the sensor unit 103 and hub 105.

In various embodiments, a personal area network communication (for example, between the multiple sensor devices and hub(s)) may be distinct from the communication between the hub 105 and the server 107. This is because the server 107 may be a remote cloud server. In this embodiment, the server 107 may not be provided on a personal area network with the hub 105 and sensor units 103. The server 107 then may be accessed by the hub 105 using an internet connection.

The hub 105 may be set up by a manufacturer to perform in a particular way. The hub 105 may also be updated with customizations to aid in the functionality of the system or a manufacturer may push firmware (or other) updates through the system to the hub 105 or sensor unit(s) 103. Optimization may involve the frequency in which a hub 105 sends information to a server 107. For example, the hub 105 may send information to the server 107, which may include the sensor information and identifying information, along with a hub identifier, once every fifteen seconds. The hub may or may not store some of the data it is sent by the sensor unit 103. For example, in the event of an internet service outage preventing uploading to the server 107, the hub 105 may continue to receive and store several hours of data and send the data to the server 107 when the outage is fixed. In order to facilitate this storage, the hub may have both volatile and non-volatile memory, such as both random access memory (RAM) and a secure digital memory card (SD card).

The hub 105 may be configured in various ways to upload bundled sensor information to the server 107 (step S207). The hub 105 may be configured to allow two-way communication between the server 107 and the hub 105. Various security measures may be required for this implementation. For example, a user may create a virtual private network (VPN) to communicate between the hub 105 and server 107 in a secure manner. The hub 105 may use a network; the hub 105 may be configured with the wireless name and password. This may include a guest wireless network; in that instance the hub 105 may be configured with a login script to get the password. In various embodiments, the hub 105 may use a cellular hotspot having login data. The hub 105 in these instances is programmed sufficiently to establish an internet connection. Configuration may be made, for example, by plugging the hub 105 into a laptop or other computer using a universal serial bus (USB) or Ethernet connection. In another embodiment, the hub 105 may create an ad hoc network for configuration. By connecting to the hub 105, the user may be provided with means to provide the hub with configuration details such as a network name and password. Once it is configured, the hub 105 may have lights such as light-emitting diodes (LEDs) to indicate certain information such as hub 105 connectivity status. The lights may be programmed to blink, change color, or any other means to create message codes.

The server 107 may receive the sensor data provided by the hub 105 at regular intervals, for example, every fifteen seconds. At a general level, the server 107 may be configured to analyze the data packet contents sent by the hub 105 in step S209 and also, in step S211, send the data to a user-facing dashboard 111 or data analytics engine 109. The server may determine whether to alert, or otherwise send a report in step S211.

Figure 4:
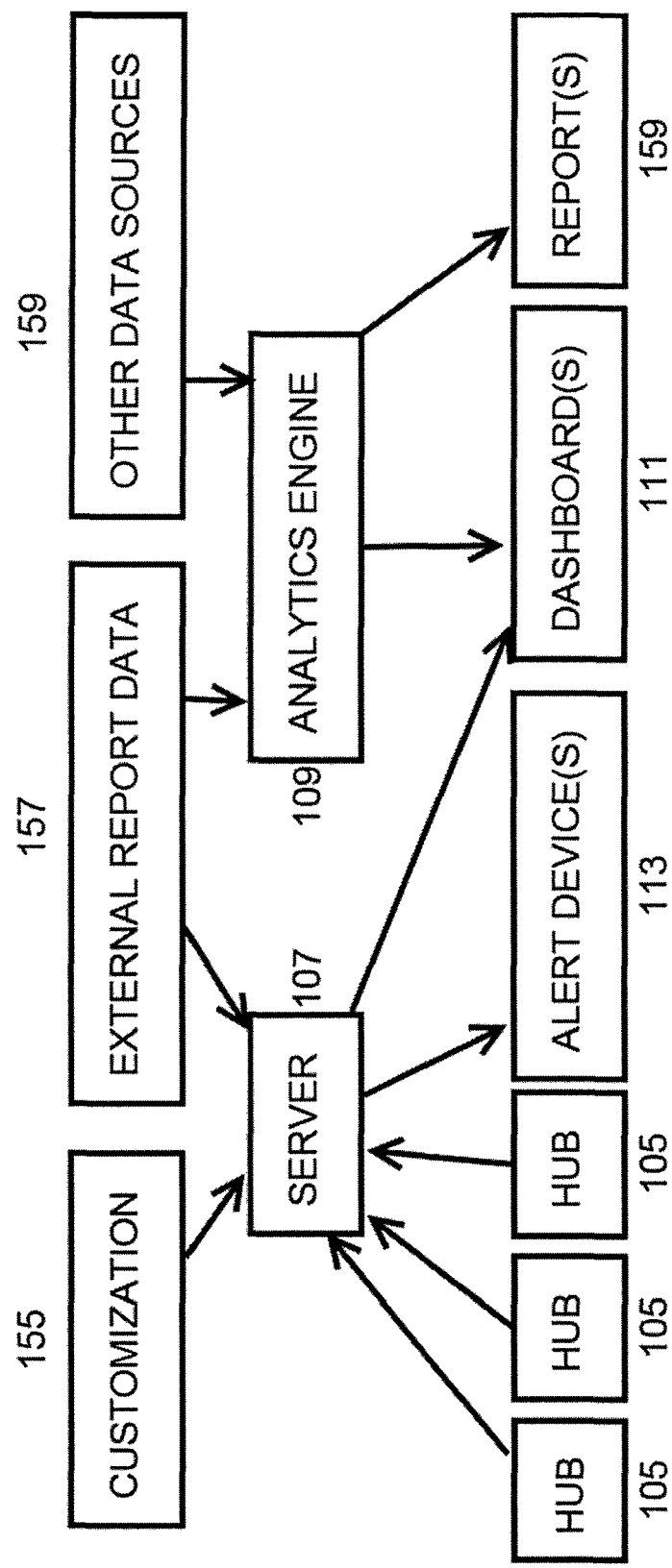
FIG. 4 is an example relationship between an example server and example data analytics engine of the disclosed system.

FIG. 4 shows an example relationship between the server 107 and data analytics engine 109. The server 107 accepts customization 155 and other inputs from a user (for example, setting a sensor unit 103 to be in an unoccupied room or alter the sensor unit's environmental context settings). The server 107 may optionally also accept external report data 157 (or the external report data may be accepted by the analytics engine 109). Unlike the data analytics engine 109, the server 107 receives data from the hub 105 and alerts the alert device 113. Both the server 107 and analytics engine 109 communicate with the dashboard. The data analytics engine 109 may optionally produce a detailed report 159 and historical data from other sources.

Figure 5:
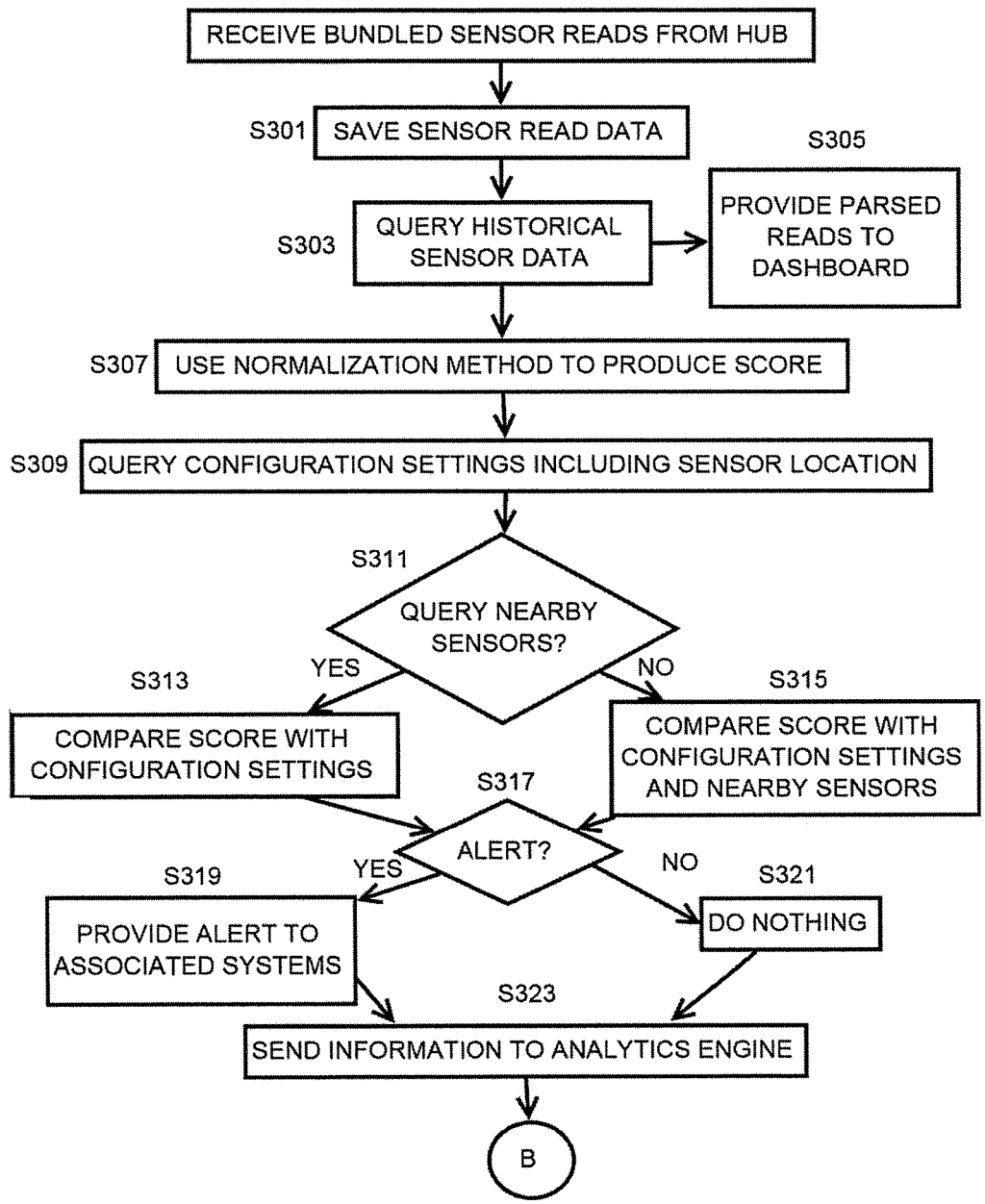
FIG. 5 is an example logic flow of an example server for use with the system disclosed.

FIG. 5 shows an example workflow of the server 107. First, FIG. 5 shows the bundled sensor reads are received from the hub 105. In various embodiments, the reads include sensor data from multiple sensors including sound, temperature, and light sensors. The sensor data also, as previously described includes a unique identifier 123 and time stamp information. By analyzing the packet contents, the server 107 can determine whether a particular sensor device 103 has stopped functioning or has limited connectivity, based on the time stamp frequency associated with the unique device identifier 123. The server 107 may also detect abnormal reads and dropped packets.

Next, the server 107 may save the new sensor read data S301 for active and historical purposes. As shown in step S303, the server 107 queries historical sensor data—the system, in various embodiments, uses a change in data to predict disruption or damage. As such, the active current values read by the sensors may be less important than the historical context or environment. Historical data interpreted in conjunction with the recently obtained data may indicate the development of a positive or negative trend.

In step S305 the interpreted data may be provided to a user dashboard 111. In various embodiments, the sensor reads may need to be changed from raw values to values a user more easily can understand. The dashboard 111 may be a graphical user interface allowing the user to view sensor data based on sensor unit 103 or hub 105 locations. The sensor device 103 or hub 105 location may be determined and transmitted by the server 107 or other system component by way of associating the unique device number 125 with the particular sensor unit 103 or hub 105 as configured in its location. The dashboard 111 may allow the user to see historical data results across the system implementation. For example, a user may be able to display visually the historic sensor data trends over a period of months. The historic sensor data may be displayed across all installed sensor units 103 or hubs 105 and associated with all hubs within the system installation. Likewise, a dashboard may be provided for those with broader access abilities, for example, allowing a regional healthcare administrator to see the sensor trends across many hospitals.

Looking to step S307, in the example of a data packet containing sound information obtained from a sound sensor 117, the sound information may be normalized using a normalization formula. In various embodiments, a novel way of quantifying the amount of sound over a reference level is used ("score"). For example, if a sound level (for example a decibel input) is obtained from a room and a threshold sound level value set, a "score" may be determined as, in various embodiments, the difference between the sound level input and a maximum allowable sound level.

This normalized value may be used to compare sound data packet information to produce a "score" or meaningful differentiation between disruptive and non-disruptive sound levels. Where the reference decibel is the maximum allowable sound level, the score represents the duration and intensity of sound above the maximum allowable decibel level for any user-defined period of time in any user-defined location or locations. The practical effect of using this method is an improvement over the current method of average decibel level using sample readings. Unlike existing methods, this "score" allows the comparison of a value over the desired sound level over various periods of time or various locations. By comparing with historical values, trends are revealed allowing users to make change necessary to affect those trends. The trends may be used by the data analytics engine 109.

In step S309, configuration and sensor unit 103 or hub 105 locations may be obtained. For example, a sound may be disruptive in one context (a hospital room around 1:00 AM) than another (a public area around 3:00 PM). Such nuances may be saved in the server 107 data storage of configuration settings 151 associated with the particular system installation or sensor device (unit or hub) 103/105. The configuration settings 151 may also have adjusted threshold levels depending on location of the sensor unit (public place versus private room, outdoor versus indoor).

Depending on the configuration settings, the server 107 may query one or more nearby sensor units 103 or hubs 105 for sensor data in step S311. By querying for nearby sensor data, if the threshold for alert for one sensor is higher (for example, louder sounds may be allowed in a public area versus room; colder temperatures may be allowed in an outdoor space versus indoors), the disruption may still impact a sensor unit in a different location (for example, noise in a public area may disrupt a bedroom). Whether or not nearby sensor units 103 or hubs 105 are queried for sensor data, the server 107 may still query configuration settings S313, S315. The server 107 may then determine whether or not to alert S317. If the server 107 determines no alert should be sent, the system may do nothing S321. If the server 107 determines the readings warrant an alert, an alert will be provided to associated systems S319. Associated systems may include cellular phones which may receive an alert in the form of a text message, a dashboard as described above which may display alerts, or any other appropriate means. For example, the sensor device 103 or hub 105 may have audio or visual means for transmitting an alert such as a beep or blinking lights.

Figure 9:
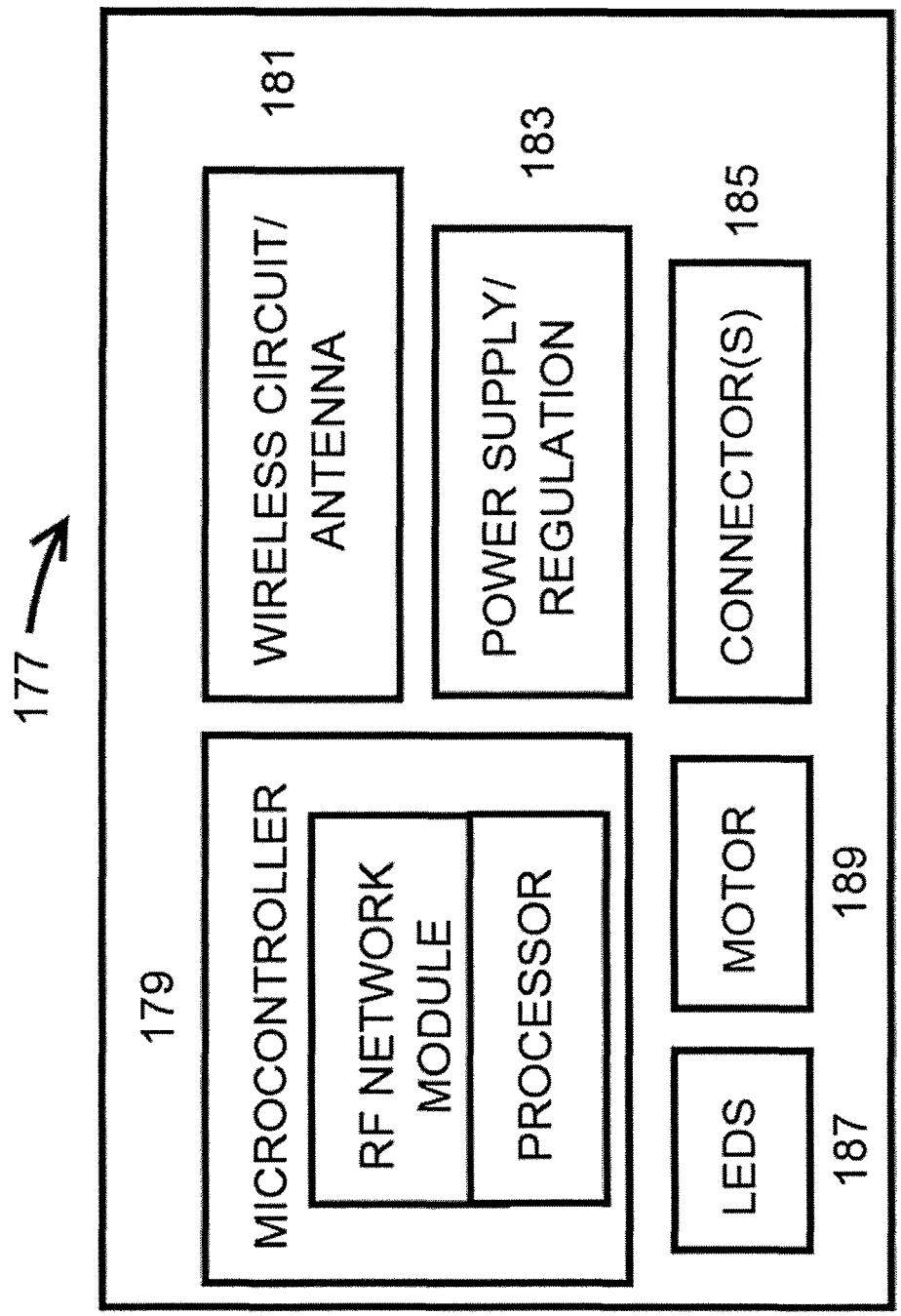
FIG. 9 is a block schematic representation of an example alert fob.

An example alert device may be an independent fob 177 worn by personnel. An example of the components of the fob 177 is provided in FIG. 9. The fob 177 may have an encasement. The encasement may be made of any suitable material, for example, plastic. The fob 177 may have a spring clip for attachment to a shirt, a hole for a lanyard attachment, or any other suitable attachment means. The fob 177 may include a microcontroller 179 which may include a radio frequency (RF) network module and processor. The fob may further include devices such as, but not limited to, a wireless circuit and/or antenna 181, a power supply/regulation 183, connector(s) 185, LEDs 187, and a motor 189. In various embodiments, the fob 177 may vibrate or provide other ways to alert a wearer of an active or potential disruption. The vibration may be enabled by the motor 189. In various embodiments, the microcontroller 179 having the RF module and/or wireless circuit/antenna 181 may be an end-point network device used with a Zigbee or Bluetooth personal wireless network. In various embodiments, details as to battery life, connectivity, or other messages may be communicated by the fob 177 using LEDs 187. The power supply and regulation 183 as well as connectors 185 may allow the fob 177 to connect to power (such as a battery) and/or charging sources using any suitable means such as, but not limited to, a USB connection (standard, micro, mini, etc.), rail charging system, and/or induction system (for example, a wireless induction system). In a non-limiting example of a rail charging system, the fob 177 or fobs may be clipped onto a specially-built charging rail, wherein the sides of the rail are charged such that when a device is clipped onto the rail(s) the clip and body contact both sides of the rail and make an electrical connection. This non-limiting example may produce more efficient charging than a wireless induction system.

In an example implementation, when the fob 177 is first turned on, it may flash one or more LEDs 187 once every few seconds to indicate that it is on but not connected to a network. The fob 177 may then connect to a network using the wireless circuit/antenna 181 and/or microcontroller 179, which may include an RF Module. The fob 179 may use an increasing frequency technique to pair with the closest sensor unit 103 or hub 105 quickly without using excess power. Once the fob 177 connects to a network (which may, in various embodiments, be the network provided by a hub 105 and/or sensor unit 103), the fob 177 may flash the LEDs 187 to indicate its connection and then stop flashing. In various embodiments, the connected hub 105 and/or sensor unit 103 may likewise be programmed to indicate a connection to a fob 177 by flashing.

The fob 177 may be used, for example, to alert a wearer when the noise levels in a room have reached a threshold. The fob 177 may, in various embodiments, regularly query its connected sensor unit 103 or hub 105 to determine whether this threshold has been reached. The fob 177 may then respond, for example, by vibrating (using a motor 189) and/or flashing (using LEDs 187) to notify a wearer of the exceeded threshold level. This may allow a wearer to abate the exceeded threshold problem before it becomes a disruption. While in this example, a sensor unit 103 or hub 105 detecting a particular area may pair directly with one or more fobs 177 in that particular area, it should be understood that information obtained throughout a network of units 103 and/or hubs 105 can be transmitted to a connected fob 177 (no matter which sensor unit 103 or hub 105 the fob 177 is connected to). As such, the fob 177 could transmit any number of different types of alerts to a wearer. For example, the fob 177 could notify the wearer of: an alert in any particular room, to check the dashboard 111 or other alert unit 113, to indicate a particular alarm code for a particular type of harm (a hospital alarm code or patient code, for example), a particular exceeded threshold (exceeded temperature or exceeded detected movement, for example), or any other suitable message. The fob 177 for example could alert the wearer with a variety of means such as vibration and blinking using its components.

Figure 6:
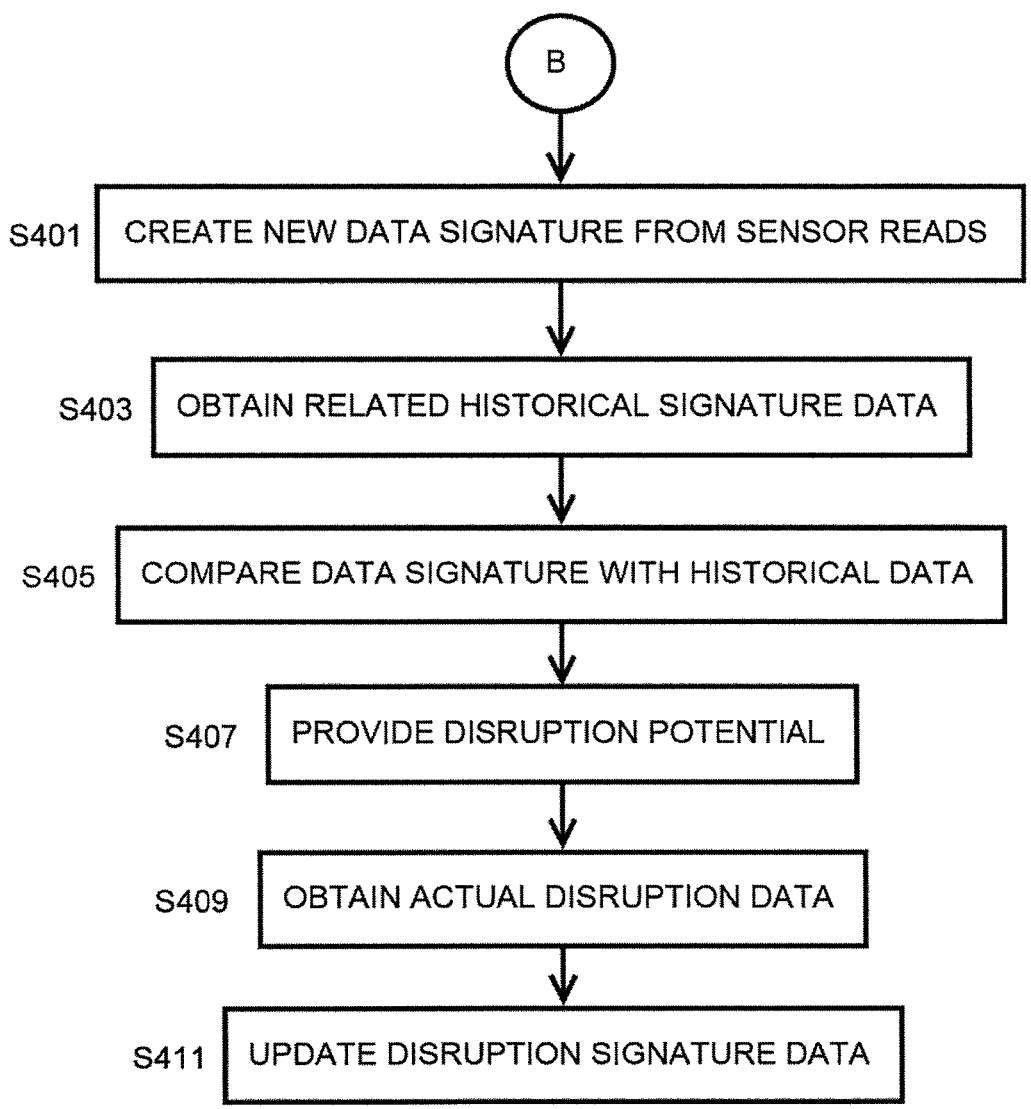
FIG. 6 is an example logic flow of an example data analytics engine of the system disclosed.

Returning to step S323 of FIG. 5, after determining whether to alert, the server 107 may send associated data to the data analytics engine 109 (though it should be understood that at any point in the logic flow of FIG. 5, data could be sent from the server 107 to data analytics engine 109). At a general level shown in FIG. 3, when the analytics engine 109 receives the data in step S213, the analytics engine 109 may, in step S215 analyze the data and possibly create a predictive report S217. This process is shown in more detail in FIG. 6. The data received from the server 107 is used to create a new data signature S401. A data signature, in various embodiments, can be a bundled results history of sensor information. The data signature may reflect a trend over a period of time. In step S403 the analytics engine 109 may obtain relevant historical signature data. This data may come from a variety of sources, including a combination of historical data reads and other data sources such as surveys. For example, the surveys may reflect whether a person felt disrupted during a period of time. The processing/analytics engine 109 will analyze the time period and correlate sensor unit data during that time to create new historical data signature information. In step S405, the data signature is compared with historical data signature information. By executing this comparison in data, the engine may use a disruption anticipation algorithm to anticipate whether or not a disruption may occur. For example, if the sound variance is similar to a disruption sound variance, though the actual decibel levels or raw read data may differ, the trend may lead to report of a disruption. Likewise, if peak noises are made at certain time intervals correlative with a non-disruptive data signature, though the decibel levels may be high, the engine 109 may predict no disruption. This disruption potential metric is provided to a user in step S407. In various embodiments, this may take the form of providing a report to an administrator or other interested party.

In step S409, actual disruption data may be obtained. In various embodiments, this may be a survey or other questionnaire given to a patient or resident that reflects their actual disruption impression. This information may be entered back into an accessible database, and the disruption signature data may be updated. In turn, the disruption signature prediction undergoes machine learning, increasing in accuracy through use of the system.

Figure 7:
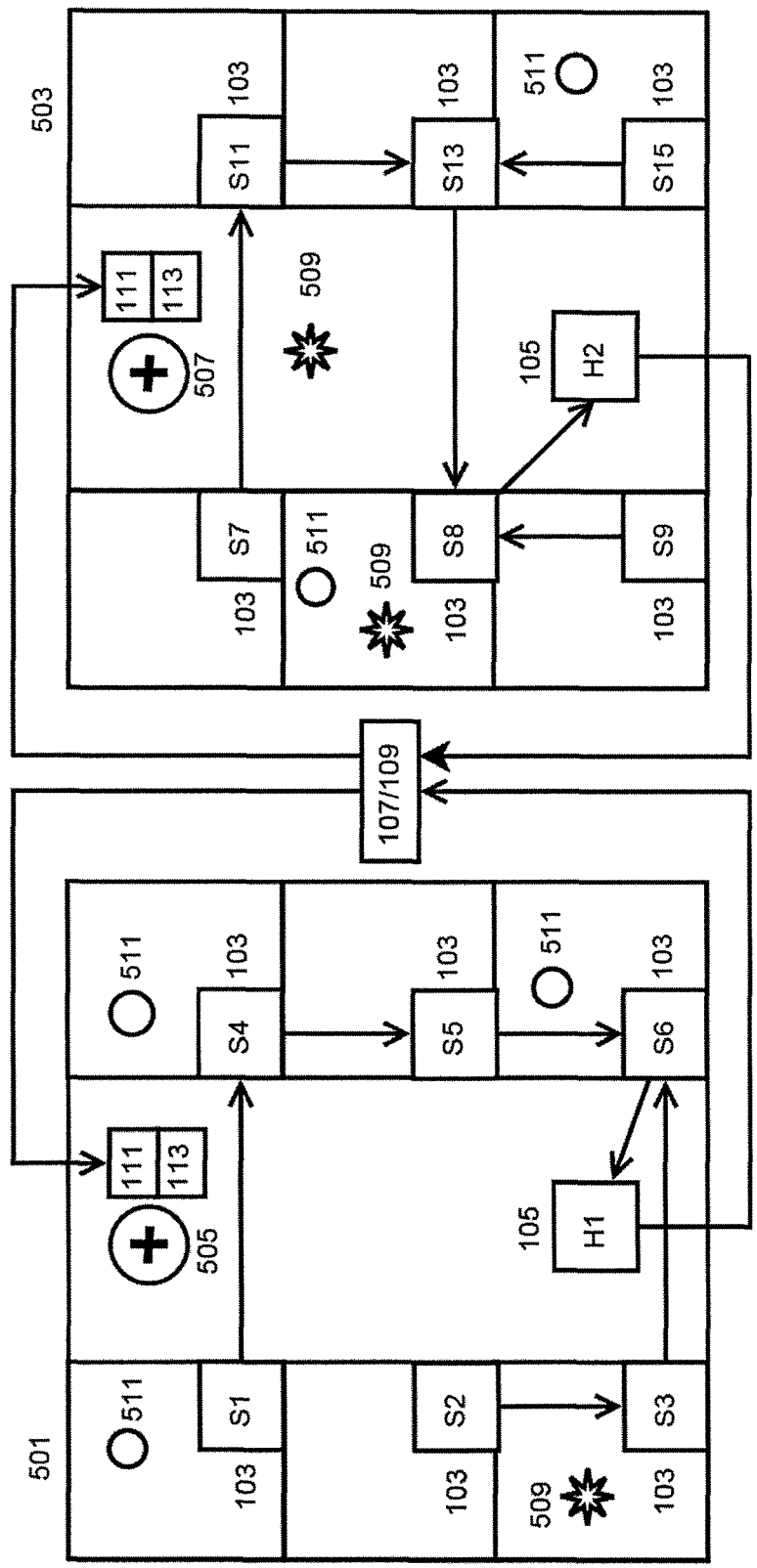
FIG. 7 is an example implementation of the system in a hospital environment.

FIG. 7 presents an example of the system implemented in a hospital. Here, two areas are shown 501/503. These areas may be on multiple floors. Each area may be provided with its own hub 105, H1 or H2. Each hub may therefore create its own wireless area network (WAN1, WAN2) throughout which the sensor units 103 and hubs 105 communicate. The example may use Zigbee-compliant devices. Therefore, communication between the sensors 103 and hub 105 is shown to use means that may or may not be compliant with a shortest-path algorithm. In this non-limiting example, each sensor unit 103 does not communicate directly with the hub 105. The example shows various noises 509, and occupied rooms 511. The example may also show a first and second nurse's station 505, 507, which may include a dashboard 111 and/or alert unit 113. The hospital may have a variety of patient rooms housing sensor units 103.

The dashboard may reflect which rooms are occupied 511 and their location. The dashboard may reflect current sensor read levels from the sensor unit 103 within the occupied or unoccupied room. In zone 1 501, a noise 509 causing a change in sound reading occurs in the lower left-hand room housing sensor unit S3. The sound reading may be sent to the hub 105, which in turn may send information to the server 107. The server 107 may determine whether the unit is occupied (it is not), whether the adjacent room experienced a change in reading, whether the adjacent room is occupied (it is not). It may calculate whether the adjacent unit showed a disruption (it did not). It may consider the main room housing the nurses' station 505 and sensor hub 105 (having sensors) in calculating the disruption. It may consider the configuration for loudness levels in the main room as compared to patient rooms (for example, higher loudness levels may be allowed in a main area rather than a patient room). It may look to whether the patient room across the main room experienced a change in readings, whether it is occupied, and whether the change constitutes a disruption. If all of these do not show a disruption, the system may or may not decide to provide an alert to the dashboard 111 or alert device 113. The system may alert personnel to determine whether a noise in an unoccupied room should be alerted to for potential equipment damage.

The noise may be considered in the production of a sleep report, which provides personnel with the number of sleep opportunities for patients overnight. Sleep opportunities may be determined, in various embodiments, as the number of times a certain sleep interval occurs per night. For example, if a sleep interval is 1.5 hours, the number of sleep opportunities in a nine hour period would be six. The system may generate a sleep opportunity report and, given its occurrence in an unoccupied room and its effect on surrounding rooms, the sound 509 may not be considered disruptive.

In contrast, in the second area 503, a change in sound reading levels 509 occurs in the main room near the nurse's station. By checking the adjacent rooms, the system can see the change is also detected in the room housing sensor unit S8. Because this unit is occupied, the system may alert the dashboard 111 and alert device 113 to alert personnel to abate the problem before it becomes disruptive. The alert device may continue to alert if the problem is not abated. In various embodiments, it may wait a certain time to re-alert. This may depend on the alert detected by the sensor—for example, if the temperature exceeds a certain threshold, it may take longer than for the violated threshold triggering the alert to be abated. Therefore, the re-alert settings may be configured accordingly.

This occurrence may be considered by the analytics engine 109 to determine whether, in the context of the readings as a whole (the data signature), a disruptive stay by the patient may be reported. After a patient leaves the hospital after their stay, they may complete a report. The report information may be entered into the system, and the prediction provided by the analytics engine 109 may be updated to reflect the actual reports.

The system and methods described herein may be implemented in or by software. To this end, the methods may be implemented in a general purpose software package or a specific purpose software package. Multiple system devices can be monitored and combined with the software application, and can be further isolated for review and evaluation.

Additional details may also be used and added to the software through one or more fields or entry points, permitting filtering or further characterization of the data obtained by the system. It is understood that the foregoing is provided for purposes of example only, and variations thereon are acceptable. For example, the application may be an application program interface (API), which provides the user the ability to customize the particular software system for the purposes or uses of the particular facility.

According to one or more examples of embodiments a variety of capabilities is provided when one or more sensors or microsystems are linked in the described system, with particularly advantageous operation being provided when a plurality of sensors or sensing microsystems are used. A variety of capabilities is also provided when the network of sensors or sensing microsystems is connected to the Internet. In addition to the foregoing, when provided access to the Internet, the system can obtain and use, or submit or otherwise provide real time or aggregated sensed data to an outside entity, such as but not limited to a utility company or other service provider, or other data destinations. In addition to data compilation, the external communication provides alarms, alerts, or other information to a user on designated device based on sensed events. Data can also be received from such an outside entity. Likewise, Internet connectivity allows for the system to receive new analysis or control algorithms or other software/firmware upgrades, as well as data usable by the system, such as current and forecasted weather information for inclusion in processing by the predictive algorithm. Internet or remote connectivity also permits the system to receive user commands from the user's computer, network-device, smartphone, or other stationary or portable data communication device. While specific examples are provided, a variety of other useful functions are enabled by network connectivity.

As described herein, in one or more examples of embodiments, the system, method, and devices described, or method embodied by software, may be implemented by a computer system or in combination with a computer system. The computer system may be or include a processor. The computers for use with the methods and various components described herein may be programmable computers which may be special purpose computers or general purpose computers that execute the system according to the relevant instructions. The computer system can be an embedded system, a personal computer, notebook computer, tablet computer, server computer, mainframe, networked computer, handheld computer, personal digital assistant, workstation, and the like. Other computer system configurations may also be acceptable including, smartphones, cell phones, mobile devices, multiprocessor systems, microprocessor-based or programmable electronics, network PC's, mini-computers, and the like. Preferably, the computing system chosen includes a processor suitable in size to efficiently operate one or more of the various systems or functions.

The system or portions thereof may also be linked to a distributed computing environment, where tasks are performed by remote processing devices that are linked through a communications network. To this end, the system may be configured or linked to multiple computers in a network, including, but not limited to a local area network, a wide area network, a wireless network, and the Internet. Therefore information and data may be transferred within the network or system by wireless means, by hardwire connection or combinations thereof. Wireless communication may be by Wi-Fi, Bluetooth, RF, and other now known or future developed means. The sensors or microsystems are each configured to communicate using a wireless communication protocol such as Wi-Fi, ZigBee, or Z-Wave. The wireless communications among the multiple sensing sensors or microsystems can be achieved in a networked fashion using a wireless router, on an ad hoc or peer-to-peer basis, various combinations thereof, or any other method that can be used to achieve wireless communication.

The computer can also include a display, provision for data input and output, etc. Furthermore, the computer or computers may be operatively or functionally connected to one or more mass storage devices, such as, but not limited to a database. The database and/or server(s) may be local or cloud based. The memory storage can be volatile or non-volatile and can include removable storage media. The system may also include computer-readable media which may include any computer readable media or medium that may be used to carry or store desired program code that may be accessed by a computer. The invention can also be embodied as computer readable code on a computer readable medium. To this end, the computer readable medium may be any data storage device that can store data which can be thereafter read by a computer system. Examples of computer readable medium include read-only memory, RAM, CD-ROM, CD-R, CD-RW, magnetic tapes, and other optical data storage devices, memory cards, USB flash drives, solid-state drives, etc. The computer readable medium can also be distributed over a network coupled computer system so that the computer readable code is stored and executed in a distributed fashion.

These devices include a graphical user interface (GUI) or a communication means by which commands may be entered and content, notification, and alerts may be displayed or communicated. For example, the computer may include a user interface that allows navigation of objects. The computer may implement or include an application that enables a user to display and interact with text, images, videos, data, and other information and content.

Aspects of the system and method described herein can be implemented on software running on a computer system. The system or method herein, therefore, may be operated by computer-executable instructions, such as but not limited to program modules, executable on a computer. Examples of program modules include, but are not limited to, routines, programs, objects, components, data structures and the like which perform particular tasks or implement particular instructions. The software system may also be operable for supporting the transfer of information within a network.

The systems and devices described may include physical hardware and firmware configurations, along with hardware, firmware, and software programming that is capable of carrying out the currently described methods. A person skilled in the art would understand that the physical hardware and firmware configurations and the hardware, firmware, and software programming that embody the physical and functional features described herein can be implemented without undue experimentation using publicly available hardware and firmware components and known programming tools and development platforms.

It is further contemplated that the system may be further arranged with objects or devices capable of performing tasks including, but not limited to: operating the one or more physical environment systems according to a schedule and sensed occupancies; providing a user interface for easy modification; providing feedback on the user display regarding occupant usage and usage patterns; learning about the preferences, habits, and occupancy patterns of the building occupants by virtue of sensor detection patterns; adapting to the learned preferences, habits, and occupancy patterns by static and/or dynamic modification; modeling or otherwise characterizing one or more capabilities of the system and its components; and optimizing the system based on the determined characteristics or data of the physical environment and/or the learned occupant preferences, habits, and occupancy patterns.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that references to relative positions (e.g., "top" and "bottom") in this description are merely used to identify various elements as are oriented in the figures. It should be recognized that the orientation of particular components may vary greatly depending on the application in which they are used.

For the purpose of this disclosure, the term "coupled" means the joining of two members directly or indirectly to one another. Such joining may be stationary in nature or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It is also important to note that the construction and arrangement of the system, methods, and devices as shown in the various examples of embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements show as multiple parts may be integrally formed, the operation of the interfaces may be reversed or otherwise varied, the length or width of the structures and/or members or connector or other elements of the system may be varied, the nature or number of adjustment positions provided between the elements may be varied (e.g. by variations in the number of engagement slots or size of the engagement slots or type of engagement). The order or sequence of any process or method steps may be varied or re-sequenced according to alternative embodiments. Other substitutions, modifications, changes and omissions may be made in the design, operating conditions and arrangement of the various examples of embodiments without departing from the spirit or scope of the present inventions.

While this invention has been described in conjunction with the examples of embodiments outlined above, various alternatives, modifications, variations, improvements and/or substantial equivalents, whether known or that are or may be presently foreseen, may become apparent to those having at least ordinary skill in the art. Accordingly, the examples of embodiments of the invention, as set forth above, are intended to be illustrative, not limiting. Various changes may be made without departing from the spirit or scope of the invention. Therefore, the invention is intended to embrace all known or earlier developed alternatives, modifications, variations, improvements and/or substantial equivalents.

The technical effects and technical problems in the specification are exemplary and are not limiting. It should be noted that the embodiments described in the specification may have other technical effects and can solve other technical problems.

The invention claimed is:

1. A disturbance detection, predictive analysis, and handling system comprising:
    a first sensor unit provided in a first location comprising a first room in a building having a sound-level sensor for obtaining sound data and one or more network communication devices, the first sensor unit programmed to transmit light, temperature and humidity data and sound-level data including a first example sound level value using the network communication device;
    a second sensor unit provided in a second location comprising a second room in the building that is nearby the first sound-level sensor, the second sensor unit having a sound-level sensor for obtaining sound-level data and one or more network communication devices, the second sensor unit programmed to transmit light, temperature and humidity data and sensor sound-level data including a second example sound level value, using the one or more network communication devices;
    a hub having one or more network communication devices, a processor, and data storage component, wherein the processor is programmed to accept and transmit the first example sound level and the second example sound level;
    a server having a network communication device, processor, and database, wherein the processor is programmed to analyze the sensor unit data; and
    a reporting device having a reporting software, the reporting device having a network communication device;
    wherein the network communication devices of the sensor unit, hub, and reporting device are selected from the group of Zigbee, Bluetooth, Wi-Fi, mobile broadband modem, or Ethernet; and
    wherein the server processor is programmed to:
    analyze the first example sound level and assign a first score based on a difference between sound level input and a maximum allowable sound level representing the duration and intensity of sound above the maximum allowable decibel level for a period of time;
    analyze the second example sound level and assign a second score based on a difference between sound level input and a maximum allowable sound level representing the duration and intensity of sound above the maximum allowable decibel level for the period of time;
    compare the first sensor unit example sound level data, first location, second sensor unit example sound level, second location, first score, and second score in addition to historical data and indication of presence or occupancy to determine whether a disruption has occurred; and wherein the server further receives a bundled results history of sound-level sensor information including the first example sound level and second example sound level and generates a first data signature and compares the first data signature to a second data signature to anticipate a disruption.

2. The disturbance detection, predictive analysis, and handling system of claim 1, further comprising a data analytics engine having a database and processor, the processor being programmed to compare the first sensor unit sound data and second sensor unit sound data with a database of historical disruption data.

3. The disturbance detection, predictive analysis, and handling system of claim 1, wherein multiple associated hubs are used.

4. The disturbance detection, predictive analysis, and handling system of claim 3, wherein a wireless area network is used to communicate between the first sensor unit and second sensor unit and multiple associated hubs.

5. The disturbance detection, predictive analysis, and handling system of claim 4, wherein the network transmission mechanisms of the first sensor unit and second sensor unit and multiple associated hubs are Zigbee compliant or Bluetooth compliant devices.

6. The disturbance detection, predictive analysis, and handling system of claim 1, wherein the first sensor unit also includes one or more of a temperature sensor, humidity sensor, or light sensor to determine the likelihood that the excessive sound constitutes a disturbance; wherein disturbance is defined as a sound with origins outside a location that can be heard within the location at specific times of day.

7. The system of claim 1, wherein the server processor is further programmed to compare the first sensor unit sound data, first location, second sensor unit sound data, and second location against a predetermined alert threshold.

8. A disturbance detection, predictive analysis, and handling system, the system comprising:
   a first networked device including a sound-level sensor in a first location, the first location comprising a first room in a building;
   a first group of sensor reads obtained by the first sound-level sensor including a highest sound level over a period of time;
   a first example sound level value determined from the first group of sound-level sensor reads obtained using the first networked device;
   a second networked device in a second location including a second sound-level sensor, the second location comprising a second room in the building;
   a second group of sensor reads obtained using the second sound-level sensor including a highest sound level over the period of time;
   a second example sound level value determined from the second group of sensor reads obtained using the second networked device;
   a server which receives the first example sound level value and second example sound level value, the server adapted to
   analyze the first example sound level value and second example sound level value in the context of the first location, second location, one or more configuration settings, and the one or more sound level thresholds;
   assign a score based on a difference between sound level input and a maximum allowable sound level representing the duration and intensity of sound above the maximum allowable decibel level for a period of time;

wherein the server further receives a bundled results history of sound-level sensor information including the first example sound level and generates a first data signature and compares the first data signature to a second data signature, wherein the first and/or second data signature may comprise a trend of sensor information over a period of time to anticipate a disruption.

9. The method of claim 8, wherein the transmission of the first example sound level value and the second example sound level value from the first and second networked devices to a first hub device is made using a personal area network.

10. The method of claim 9, wherein the personal area network is a Zigbee compliant and/or Bluetooth compliant network.

11. The method of claim 8, further comprising:
   providing a first unique identifier with the first example sound level value by the first networked device to the first hub device;
   providing a second or higher unique identifier with the second example sound level value by the second networked device to the first hub device;
   associating the first example sound level value with the first location by using the first unique identifier; and
   associating the second or higher example sound level value with the second location by using the second unique identifier; and
   considering sound level values of nearby networked devices before determining whether to alert.

12. The method of claim 8, further comprising:
   transmitting the first example sound level value and second example sound level value to a data analytics engine;
   analyzing the first example sound level value and first data signature and second example sound level value and second data signature against the database of historical disruption data using the data analytics engine.

13. The method of claim 12, further comprising:
   creating a historical disruption signature using the historical disruption data and externally-provided data;
   comparing the first example sound level value and second example sound level value against the historical disruption signature to anticipate a disruption.

14. The method of claim 8, wherein the first example sound level value is the highest decibel read obtained by the sound sensor within the first period of time.

15. The method of claim 8, wherein the alert device is a data alert fob.

16. The method of claim 8, further comprising: obtaining user feedback data over a period of time and incorporating the user feedback data into the historical disruption data.

17. A method of claim 8, further comprising:
   obtaining a plurality of sound level inputs and a timestamp from the sound sensors;
   comparing the decibel inputs with a maximum allowable sound level;
   saving the score and timestamp;
   continuing to save scores and timestamps to create historic values; and
   comparing a new score against the historic values.

18. An improved disturbance detection, predictive analysis, and handling method, the method comprising:
   obtaining a plurality of first sound-level sensor reads from a first sound-level sensor in a first location comprising a first room in a building;

determining a first example sound value from the plurality of first sound sensor reads comprising a first highest sound level value;

comparing the first example sound value with a database containing configuration settings;

obtaining a plurality of second sound-level sensor reads from a second sound-level sensor in a location comprising a second room in the building that is in nearby the first sound-level sensor;

determining a second example sound-level value from the plurality of second sound sensor reads comprising a second highest sound level value;

assigning a score based on a difference between sound level input and a maximum allowable sound level representing the duration and intensity of sound above the maximum allowable decibel level for a period of time;

determining if the first location and/or second location is occupied;

generating a first data signature based on a bundled results history of sound-level sensor information including the first example sound level and comparing the first data signature to a second data signature to anticipate a disruption;

saving the first example sound level value and second example sound level value to a database to create historical disruption data.

19. The method of claim 18, wherein the first location is a first patient or occupant room at a hospital, assisted living, hospitality, residential, or facility and the second location is a second patient or occupant room at a hospital, assisted living, hospitality, residential or facility.

* * * * *